United States Patent
Hachenberg et al.

(10) Patent No.: US 9,321,104 B2
(45) Date of Patent: Apr. 26, 2016

(54) DEVICE AND METHOD FOR SINTERING SINTER PRODUCTS

(71) Applicants: Joerg Hachenberg, Aschaffenburg (DE); Rudi Steinke, Hanau (DE); Peter Popp, Omersbach (DE); Irmgard Wissel, Freigericht (DE)

(72) Inventors: Joerg Hachenberg, Aschaffenburg (DE); Rudi Steinke, Hanau (DE); Peter Popp, Omersbach (DE); Irmgard Wissel, Freigericht (DE)

(73) Assignee: DEGUDENT GMBH, Hanau (DE)

( * ) Notice: Subject to any disclaimer, the term of this patent is extended or adjusted under 35 U.S.C. 154(b) by 482 days.

(21) Appl. No.: 13/709,213

(22) Filed: Dec. 10, 2012

(65) Prior Publication Data

US 2013/0149186 A1 Jun. 13, 2013

(30) Foreign Application Priority Data

Dec. 9, 2011 (DE) .......................... 10 2011 056 211

(51) Int. Cl.
| | |
|---|---|
| *C21D 9/00* | (2006.01) |
| *B22F 3/00* | (2006.01) |
| *B22F 3/10* | (2006.01) |
| *F27B 5/04* | (2006.01) |

(Continued)

(52) U.S. Cl.
CPC ............... *B22F 3/003* (2013.01); *B22F 3/1007* (2013.01); *F27B 5/04* (2013.01); *F27B 5/10* (2013.01); *F27B 14/04* (2013.01); *F27B 17/025* (2013.01); *F27D 5/0043* (2013.01); *A61C 13/20* (2013.01)

(58) Field of Classification Search
CPC ....... C03B 37/0146; F27B 21/00; F27B 5/04; F27B 5/00
USPC ............ 432/81, 258, 254.1, 254.2, 252, 247, 432/262; 206/454; 148/527; 264/16
See application file for complete search history.

(56) References Cited

U.S. PATENT DOCUMENTS 4,189,129 A * 2/1980 Engelhard ..................... 266/251
4,406,618 A * 9/1983 Maeyama ....................... 432/23

(Continued)

FOREIGN PATENT DOCUMENTS

DE 10 2008 012 578 A1 9/2009
DE 20 2010 002 533 U1 7/2010

(Continued)

OTHER PUBLICATIONS

Chinese Search Report issued Mar. 4, 2015, corresponding to Chinese Patent Application 2012105220244.

(Continued)

*Primary Examiner* — Gregory A Wilson
(74) *Attorney, Agent, or Firm* — Ladas & Parry LLP

(57) ABSTRACT

The invention relates to a device (10) and a method for sintering sinter products, such as oxidation-prone materials, in particular metallic sintered goods (46), in particular a dental framework, comprising a tray (18), which accommodates the sinter product and is arranged on a base plate (14), a pot-shaped cover (16), which surrounds the tray, with a rim (36) that is sealed towards the base plate, as well as supply and discharge openings (38) for protective gas connected to the interior chamber (30) that is surrounded by the pot-shaped cover. In order to facilitate sintering even at temperatures above 1200° C. without any problems, it is suggested that the tray (18) be covered by a capping element (20), whereby when the tray is covered by the capping element, the interior chamber (34) of the tray is connected in a gas-flow-allowing manner to the interior chamber of the cover.

14 Claims, 2 Drawing Sheets

(51) Int. Cl.
  *F27B 5/10*   (2006.01)
  *F27B 14/04*  (2006.01)
  *F27B 17/02*  (2006.01)
  *F27D 5/00*   (2006.01)
  *A61C 13/20*  (2006.01)

(56) References Cited

U.S. PATENT DOCUMENTS

| | | | |
|---|---|---|---|
| 4,855,101 A | | 8/1989 | Mohs et al. |
| 5,362,438 A | | 11/1994 | van der Zel |
| 5,755,570 A | * | 5/1998 | Shinde et al. ............... 432/253 |
| 8,591,803 B2 | | 11/2013 | Wolff et al. |
| 2003/0031974 A1 | * | 2/2003 | Takagi .......................... 432/253 |
| 2006/0029897 A1 | * | 2/2006 | Saijo et al. .................... 432/121 |
| 2008/0197544 A1 | * | 8/2008 | Saijo et al. .................... 264/671 |

FOREIGN PATENT DOCUMENTS

| | | |
|---|---|---|
| DE | 20 2010 007 606 U1 | 9/2010 |
| DE | 202010007606 U1 | 10/2010 |
| DE | 20 2011 005 465 U1 | 6/2011 |
| DE | 202011005465 U1 | 8/2011 |
| DE | 20 2011 106 734 U1 | 11/2011 |
| EP | 0 524 438 A2 | 1/1993 |
| EP | 0524438 A2 | 1/1993 |
| EP | 2 101 133 A1 | 9/2009 |
| EP | 2098188 A1 | 9/2009 |
| EP | 2101133 A1 | 9/2009 |
| JP | 2002-372373 A | 12/2002 |
| WO | 94/16642 A1 | 8/1994 |

OTHER PUBLICATIONS

Die vierte Nationale Konferenz mit Beitragen zu einem Thema der Fluidabdichtungstechnik, Zhirong Zheng, Jan. 16, 2006; cited in Chinese Search Report issued Mar. 4, 2015, corresponding to Chinese Patent Application 2012105220244.

Search Report dated Mar. 28, 2013 for Application No. EP 12 19 4369.

Espacenet English abstract of JP 2002-3723743 A.

* cited by examiner

DEVICE AND METHOD FOR SINTERING SINTER PRODUCTS

This application claims priority to German patent application number 10 2011 056 211.7, filed Dec. 9, 2011, the contents of which are incorporated by reference herein.

BACKGROUND OF THE INVENTION

The invention relates to a device for sintering sinter products, comprising a tray accepting the sinter products that is arranged on a base plate, an interior chamber accommodating the sinter products as first interior chamber, a pot-shaped cover, which surrounds the tray and possesses a rim that is sealed towards the base plate, with a protective-gas supply and discharge opening connecting to an interior chamber encompassed by the pot-shaped cover as the second interior chamber, as well as a sintering chamber, which surrounds the pot-shaped cover and the base plate, as the third interior chamber.

The invention further relates to a method for sintering sinter products, such as materials prone to oxidation, in particular metallic sinter products, in particular in form of a dental framework, using a device that comprises a tray arranged on a base plate, with an interior space that accepts the sinter products as the first interior chamber, a pot-shaped cover, which encompasses the tray and has a rim that is sealed towards the base plate, as well as openings for discharge and supply of protective gas connecting to the interior chamber that is surrounded by the cover as the second interior chamber, whereby protective gas flows through the second interior chamber surrounded by the pot-shaped cover.

A device and method of the above-mentioned type are described in DE 20 2010 007 606 U1 and DE 20 2010 002 533 U1. For this purpose, dental frameworks consisting of a silver palladium alloy or chromium cobalt alloy are sintered in a tray, which consists of quartz and is supported at elevation on a fireclay block in a sintering furnace. The fireclay block and the tray are surrounded by a quartz vessel that is sealed by a graphite gasket towards a base plate, on which is arranged the fireclay block. Both the base plate and the fireclay block have bore-hole openings, in order to be able to flush the interior chamber, which contains the quartz tray and is surrounded by the quartz vessel, with a protective gas such as argon. In order to prevent oxidation of the frameworks, the sintering is performed in a protective gas atmosphere. Since an undesirable corrosion of the quartz takes place at temperatures around 1200° C., one coats this in advance with a boron nitride spray. The material to be sintered is placed in the tray of inert pellets of corundum, alumina, or zirconia.

This device suffers from the disadvantage that it can not be used at temperatures above 1200° C.; since on the one hand the life expectancy of quartz is highly limited at these temperatures and on the other, direct contact with finger grease as a result of handling the quartz materials leads to spalling.

DE 20 2011 106 734 U1 relates to a device for the oxygen-free sintering of metal or ceramics and comprises a base plate, upon which is supported a dome. Within the dome, a sintering crucible, into which sinter products may be placed, is supported via a support plate. Also present are openings for the supply and discharge of protective gas. As suitable materials for the device are listed quartz glass or re-crystallized silicon carbide.

WO 94/16642 A1 relates to a furnace, in which is arranged a furnace chamber, which on the fore-side is covered by a lid, through which gas is allowed to flow when protective gas is introduced into the furnace chamber.

Subject matter of EP 2 101 133 A1 is a sintering furnace for dental preparations.

DE 10 2008 012 578 A1 relates to a dental furnace, which is used to perform various heating cycles. An overshoot of the heating output may occur during this.

DE 20 2011 005 465 U1 relates to a device for the oxygen-free sintering of metal or ceramics. In this, the product to be sintered in a sintering container is embedded in sintering granules, which for example may consist of zircon granules.

SUMMARY OF THE INVENTION

An objective of the present invention is to further develop a device and a method of the above-mentioned type in such a way that the disadvantages of the state of technology are avoided, and in particular a sintering at temperatures above 1200° C. can be performed without any problems. At the same time it should be ensured that undesired discoloration or oxidation of the sinter products are ruled out.

With respect to the device this objective is essentially met by the tray being covered by a capping element, and that the first interior chamber is connected to the second interior chamber in a gas-flow-allowing fashion when the tray is covered by the capping element.

The invention further relates to a device for sintering of sinter products goods that comprises a tray, which accepts the sinter product, is arranged on a base plate, and possesses an interior chamber as first interior chamber that accepts the sinter product, a pot-shaped cover encompassing the tray with a rim that is sealing with respect to the base plate, with an opening for the supply and discharge of protective gas connecting to the interior space as second interior chamber surrounded by the pot-shaped cover, as well as the sintering chamber, which surrounds the pot-shaped cover with the base plate, as third interior chamber, which is characterized in that the tray is covered by a capping element, and that the first interior chamber is connected in a gas-flow admitting fashion to the second interior chamber when the tray is covered by the capping element.

In accordance with the invention's teaching, sintering of the sinter products takes place in the interior space surrounded by the tray that is referred to as first interior chamber, whereby the tray is covered by a capping element. Irrespective of this, inert gas can flow through the first interior chamber, but the risk of interference such as oxygen reaching the interior of the tray are reduced to a large degree.

It in particular is intended that the cover be supported on the base plate directly on its rim in a gas-tight or form-fitting fashion. The rim of the cover as well as the base plate are surface-ground to such a degree that the cover can rest directly on the base plate without any additional sealing, in order to obtain a sealing to such a degree that ingress of oxygen into the interior space surrounded by the cover and referred to as second interior chamber is ruled out or ruled out to a great extent.

These measures serve to ensure that no oxygen or almost no oxygen ingresses from the surroundings into the (second) interior chamber of the cover, that also may be referred to as cone, and consequently none or almost none ingresses into the (first) interior chamber surrounded by the tray.

It should also be emphasized that at least the tray and its capping element, such as a lid, but in particular the base plate, the tray, the capping element, and the pot-shaped, hood-like, or cone-shaped cover, consist of a material that is a member of the group made up of SiC, SiN. This choice of material offers the advantage that sintering can be performed at temperatures above 1200° C., in particular up to 1350° C., without the materials suffering any damage. Particularly preferred is the use of SiC, since it possesses a reducing effect with respect to oxygen.

The inert gas conducted into the space between the tray and the pot-shaped cover, which in particular should be argon but possibly may be nitrogen, in accordance with a further development of the invention can be conducted from the second interior chamber, which is encompassed by the cover, directly into the sintering chamber surrounding the base plate and the cover, i.e. into the interior space of a sintering furnace referred to as third interior chamber. This results in a further drop of the concentration of oxygen in the sintering chamber (third interior chamber) of the sintering furnace. Also, ingress of oxygen into the (second) interior chamber of the cover is impeded.

In a further development of the invention it is intended that the tray be supported on a ring that possesses openings, which in turn is arranged on a base plate, whereby preferably through the base plate inside of the ring passes the protective-gas supply-line opening and possibly the protective-gas discharge-line opening.

As an alternative it is suggested that from the tray or its bottom wall originate projections, preferably at least three projections, which are arranged uniformly around a circle and serve to support the tray on the base plate.

These measures ensure that the base plate can possess a thickness that is the same anywhere on the entire surface, so that one does not face the risk of fissuring due to the temperature changes occurring during sintering.

The invention is further characterized in that the product to be sintered is supported in the tray on bulk material that consists of solid balls of ceramics, in particular zirconium oxide or aluminum oxide. Zirconium dioxide offers the advantage that under the exclusion of oxygen this is partially converted to zirconium monoxide. The voids generated by the lack of oxygen result in a dark discoloration.

Surprisingly this initial oxygen release has no negative effect and in the following can be used in a reducing and indicating role, since this effect is reversible in case of an ingress of oxygen.

As a result of the invention's teaching one can ensure that sintering of metal alloys, in particular cobalt chromium alloys such as cobalt-chromium-molybdenum alloys, can be performed at temperatures of 1200° C. and above, in particular 1250° C., without any risk of oxidation or uncontrolled discoloration. In this, the sinter products are arranged in a tray with a capping element capping the latter, whereby it is ensured that the (first) interior chamber of the tray that accepts the sinter product is flushed with a protective gas in order to flush out any oxygen that might be present. The capping element acts in a lid-like manner or is a lid.

If in a preferred manner the capping element covering the tray is arranged on the tray in a non-sealing fashion, a sealing contact would also be possible as long as fine bore holes, e.g. created by lasers, are provided, e.g. in the capping element itself, that allow protective gas exchange.

A further option is to let protective gas—which was conducted to the outside from the (second) interior chamber of the cover—flow around the pot- or bell-shaped cover, i.e. the so-called cone.

It is in particular of advantage that the materials are suitable for high-temperature sintering, whereby silicon carbide is to be emphasized, in particular because of its reducing action. Alternatively one also can use silicon nitride.

A method of the above-mentioned type is also characterized in that the tray—after the sinter product has been placed in it—is covered by a capping element, so that through this or at least through an opening in the capping element or through an opening in the tray, protective gas can enter the interior of the tray, i.e. the first interior chamber, and that the (second) interior chamber of the pot-shaped cover is charged with protective gas at an excess pressure that rules out lifting the cover, in particular with an excess pressure p with $1 \text{ mbar} \leq p \leq 25 \text{ mbar}$, in particular $2 \text{ mbar} \leq p \leq \text{mbar}$ above ambient pressure.

In particular it is intended that as sinter product be used a larger object, in particular a dental bridge framework, in particular a bridge framework with at least three bridge elements, preferably at least five bridge elements, and that the sinter product be heated in a sintering chamber, which accommodates the device, i.e. surrounds it, from room temperature Tz to a temperature $T_1$ with $800° \text{ C.} \leq T_1 \leq 1100° \text{ C.}$ at a heating rate $R_1$ with $5 \text{ K/min} \leq R_1 \leq 100 \text{ K/min}$, in particular $20 \text{ K/min} \leq R_1 \leq 80 \text{ K/min}$, after a possible holding time $t_1$ at the temperature $T_1$ with $1 \text{ min} \leq t_1 \leq 10 \text{ min}$ is heated to a temperature $T_2$ with $1200° \text{ C.} \leq T_2 \leq 1350° \text{ C.}$ at a heating rate $R_2$ with $5 \text{ K/min} \leq R_2 \leq 30 \text{ K/min}$, the sinter product is held at the temperature $T_2$ for a time period $t_2$ with $5 \text{ min} \leq t_2 \leq 120 \text{ min}$, in particular $15 \text{ min} \leq t_2 \leq 50 \text{ min}$, whereby subsequently, i.e. after the holding time $t_2$, the sinter products possibly are heated to a temperature $T_3$ with $T_3 > T2$ to melt the surface of the sinter product, and subsequently from the temperature $T_2$ or $T_3$ is cooled to a temperature below 400° C. at a cooling rate $R_3$, which preferably at the start of the cool-down amounts to $5 \text{ K/min} \leq R3 \leq 100 \text{ K/min}$. This is followed by cooling to room temperature Tz.

The invention also intends that the sinter product be heated in a sintering chamber surrounding the device from room temperature to a temperature $T_2$ such as $1200° \text{ C.} \leq T_2 \leq 1350° \text{ C.}$ at a heating rate $R_1$, be kept at the temperature $T_2$ for a time period $t_2$ with $5 \text{ min} \leq t_2 \leq 220 \text{ min}$, in particular $15 \text{ min} \leq t_2 \leq 60 \text{ min}$, whereby possibly subsequently, i.e. after the holding time, the sinter products are heated to a temperature $T_3$ with $T_3 > T_2$ to melt the surface of the sinter product, in order to be cooled subsequently from the temperature $T_2$ or $T_3$ to a temperature above 400° C. at a cooling rate $R_3$, whereby the cooling rate $R_3$ preferably at least at the start of the cool-down is $5 \text{ K/min} \leq R_3 \leq 100 \text{ K/min}$.

In this, it in particular is intended that the heating rate $R_1$ be set to a value with $5 \text{ K/min} \leq R_1 \leq 100 \text{ K/min}$, in particular $20 \text{ K/min} \leq R_1 \leq 80 \text{ K/min}$.

The heating to a temperature $T_1$ and the possibly performed holding at the temperature $T_1$, to be subsequently further heated to a temperature $T_2$, is the preferred treatment for larger objects such as bridge frameworks.

The initially occurring heating to the temperature $T_1$ and subsequently to the temperature $T_2$ with a potentially different heating rate can be modified so that heating to the temperature $T_2$ takes place immediately, if the products to be sintered are smaller objects, such as a framework for a tooth.

In this, the short-term melting of the surface, which can be performed independently of the size of the object, represents a suggestion with its own inventive merit that may be applied even if one uses in the sintering a device that deviates from the invention's teaching.

It may be intended additionally that after cooling of the sinter products to the temperature $T_1$, the base plate with the tray, the latter's capping element, and the cover, are removed from the sintering chamber at least in parts but preferably entirely. The sintering chamber may be the interior chamber of a sintering furnace, which is referred to as the third interior chamber.

Independently of the temperatures and heating rates specified above, one has to emphasize as a feature with its own independent inventive merit that it is possible to perform an additional heating step after the dense sintering, as a result of which the surface of the sintered product melts and one achieves desired surface characteristics.

The high temperatures present in the interior of the tray for a short time period result in a melting of the surface, so that for frameworks the surface will have an appearance that is very similar to that of frameworks subjected to dental polishing.

In particular, it is intended that the protective-gas-inlet or protective-gas-discharge opening be connected to a supply or discharge line consisting of aluminum oxide. In this, the line may be connected to the base plate using a high-temperature bonding-agent, in particular on aluminum oxide basis.

In the choice of SiC as material for the base plate, the cover, the tray and its capping element one makes use of the good thermal conductivity and the nearly complete leak tightness of the material. As a result of this, temperature differences within the components are minimized, which reduces thermal stresses. Consequently, rapid temperature changes are even feasible for large components, e.g. with a diameter of 100 mm. In addition, SiC exhibits a reducing effect and is able to convert residual oxygen in the atmosphere together with the carbon present to form carbon monoxide. This effect is still in effect. But at the same time, no measurable reduction of the wall thickness can be detected.

Placing the sinter products in a sintering tray that is not closed seal-tight improves the sintering results. The reason for this improvement may be the creation of an internal chamber that possesses walls with a reducing action with respect to oxygen. The interference by oxygen is consequently attenuated. Interference of this type is not longer able to reach the sinter product directly. The probability of the interference being flushed out and consequently being moderated is higher.

The controlled supply and discharge of inert gas ensures that the internal pressure in the cover can not increase to such a degree that the latter is lifted. In this manner one facilitates the exclusion of oxygen. Instead of one or several protective gas discharge line openings in the base plate, it is possible that at least one opening formed by laser is present in the cover, in order to discharge inert gas in a controlled manner.

Deviating form conventional techniques, no hollow balls are used in the support of the sinter products. Hollow balls can store oxygen and consequently at high temperatures contaminate the atmosphere in immediate proximity to the goods to be sintered. The invention employs dense balls that can not store oxygen. In this, zirconium oxide has surprisingly been found to be suitable as material for the balls, even though initially it tends to release oxygen in low-oxygen atmospheres. After the oxygen release is complete, e.g. achieved by a temperature cycle, the corresponding solid balls of zirconium oxide exhibit a reducing effect for oxygen.

In order to position the cover and the tray in their proper positions on the base plate, the state of technology usually intends for the presence of steps. The invention breaks away from this and employs a level plate, which in a simple manner can be polished in the regions of the contact areas to the cover, so that sealing takes place to such a degree that an ingress of oxygen on principle is excluded or substantially excluded. Since no steps are present, there will be no thickness variations in the base plate, so that thermal stresses consequently are reduced.

Further details, advantages, and features of the invention are not only found in the claims, the characteristic features described therein—individually or in combination—but also in the following description of preferred embodiment examples illustrated in the figures.

DESCRIPTION OF THE PREFERRED EMBODIMENTS

Figure 1:
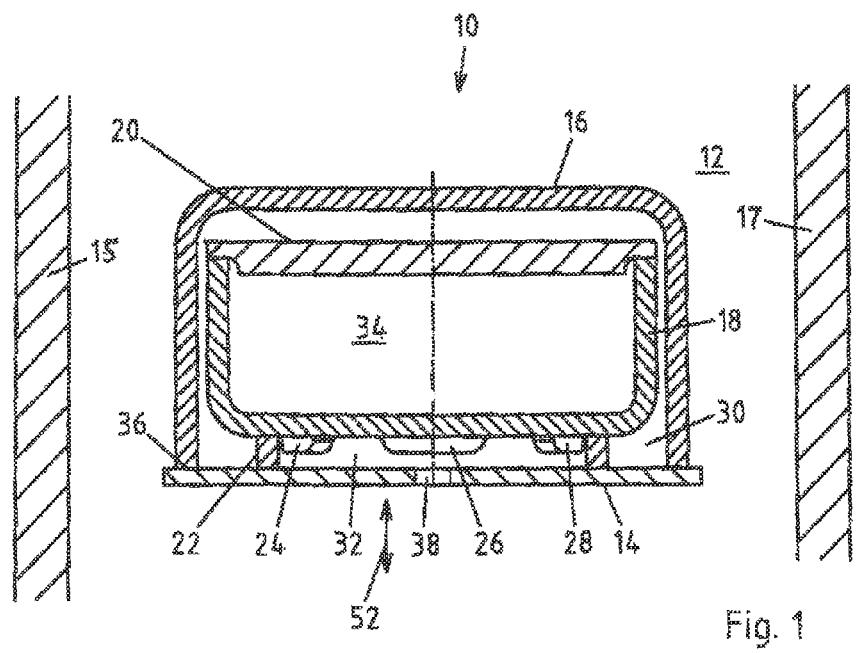
FIG. 1 shows a first embodiment variant of a device for sintering sinter products.
Figure 2:
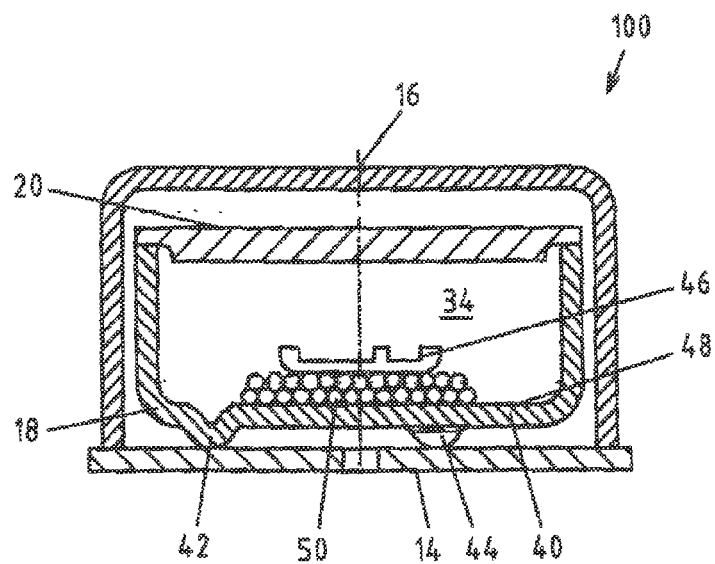
FIG. 2 shows a second embodiment variant of a corresponding device.

FIGS. 1 and 2, which on principle use identical reference labels for equal elements, show in respective purely schematic illustrations an embodiment variant of a device 10, 100 that is used to sinter metallic sinter products, in particular dental frameworks. As is schematically illustrated in FIG. 1, the device 10—and accordingly the device 100—is located in an interior or sintering chamber 12 of a sintering furnace, of which wall sections 15, 17 are schematically illustrated. In the sintering chamber 12, which is also referred to as third interior chamber, one sets the temperatures that are required to sinter to the required degree the sinter product present in the device 10, 100.

The device 10 consists of a base plate 14, a pot-shaped or dome-shaped cover 16, to be referred to as cone, a tray 18 with a U-shaped cross-section, as well as a lid 20 referred to as capping element, by means of which the tray 18 on principle is sealed in a less than complete manner.

Further, the tray 18 is supported on the base plate 14 via a ring element 22. The ring element 22 possesses cut-outs 24, 26, 28, so that a connection exists between the interior chamber 30 surrounded by the cone 16—referred to as second interior chamber—and the chamber 32 surrounded by the ring element 22. The sinter product—not illustrated in FIG. 1—is arranged in the interior chamber 34 surrounded by the tray 18 and capped by the lid 20, referred to as the first interior chamber.

According to the invention's teaching, the base plate 14, the cone 16, the tray 18, the lid 20, as well as the ring element 22, preferably are manufactured from SiC, even though SiN can be considered as an alternative material.

The base plate 14 and the circumferential rim 36 of the cone 16 have been ground flat to such a degree that one can be sure of a form-fitting contact of the cone 16 on the base plate 14. This in principle prevents the ingress of oxygen.

In accordance with the invention, the lid 20 should not completely seal the (first) interior chamber of the tray 18, so that a flow-allowing connection exists between the (second) interior chamber 30, which extends between the tray 18 and the cone 16, and the first interior chamber 34 that is surrounded by the tray 18. If the lid 20 rests upon the tray 18 in a sealing manner, then the lid 20 possesses at least one opening, so that a flushing of the interior chamber 34 of the tray 18 can take place. The equivalent would be achieved by an opening in the tray 18.

In order to prevent oxidation and discoloration, a protective gas such as argon or nitrogen is fed into the second interior chamber 30 via an opening 38 that in the embodiment example is provided in the base plate 14. This protective gas reaches the first interior chamber 34 that is surrounded by the tray 18, since, as already mentioned, the lid 20 does not close the tray 18 in a sealing manner. Alternatively or additionally the protective gas travels via the at least one opening in the lid 20 and/or in the wall of the tray 18.

The gas admitted to the second interior chamber 30 subsequently flows out via an opening that preferably is also present in the base plate 14. But it is also possible to create an opening in the circumferential wall of the cone 16, e.g. by means of a laser, through which gas discharges. In this, the out-flowing gas preferably is conducted into the sintering chamber 12—i.e. the third interior chamber—in such a manner that the protective gas flows around the cone 16 at least in the region of the latter's circumferential rim 36.

Due to the fact that the lid 20 rests on the tray 18 in a non-sealing manner, protective gas can flow into the first interior chamber 34, which is surrounded by the tray 18 and in which the sinter products are located. At the same time, the ingress of oxygen (interference) is reduced. The equivalent applies with respect to the at least one opening.

The (second) interior chamber 30 should be at a higher pressure than the surroundings, whereby an excess pressure burden between 1 mbar and 25 mbar, in particular between 2 mbar and 10 mbar is preferred.

The embodiment example of FIG. 2 differs from the one of FIG. 1 in that the tray 18 is not supported on a ring 22, but rather via projections 42, 44 that rise from the bottom wall 40 of the tray 18. In this there are provided in particular three projections that are arranged uniformly distributed around a circle. In all other respects the embodiment variant corresponds to that of FIG. 1, so that the reader is referred to the respective explanation.

Supporting the tray 18 on the ring 22 or via the projections 42, 44 realizes the advantage that the base plate 14 possesses a uniform thickness, so that one avoids thickness variations, which consequently reduces internal stresses.

In order to facilitate that during the sintering, the sinter product 46 located in the first interior chamber 34 not touch the inner surface of the tray 18, a spheroidal bulk matter 50 consisting of solid balls, i.e. not of hollow balls is introduced to the interior side 48 of the bottom wall 40, i.e. on the bottom surface. Materials that are preferred for this are aluminum oxide or zirconium oxide. The solid balls offer the advantage that oxygen can not be stored. This is also true for zirconium oxide balls, even though they initially tend to release oxygen, namely in atmospheres low in oxygen. However, after a completed oxygen release, they exhibit a reducing action.

The preferred dimensions of the components, consisting in particular of silicon carbide, are:

Base plate 14: Diameter 90 mm to 110 mm, Thickness 2 to 4 mm;
Cone 16: Outer diameter 95 mm to 105 mm, wall thickness 3 mm to 5 mm, height 50 mm to 55 mm;
Ring element 22: 4 mm to 8 mm, outer diameter 60 mm to 70 mm, wall thickness 3 mm to 5 mm;
Sintering tray 18: Height 30 mm to 35 mm, outer diameter 80 mm to 90 mm, wall thickness 3 mm to 5 mm;
Lid 20: same outer diameter as tray 18, thickness in the border region: 2 mm to 5 mm, Central thickness 4 mm to 8 mm As is apparent in the drawing, the distance between the outer surface of the tray 18 and the inner surface of the cone 16 can be chosen to be small. This offers the advantage that this additionally inhibits the ingress of oxygen into the (first) interior chamber 34 of the tray 18, in particular if the protective-gas discharge opening is located in and passes through the edge region of the cone 16.

Figure 3:
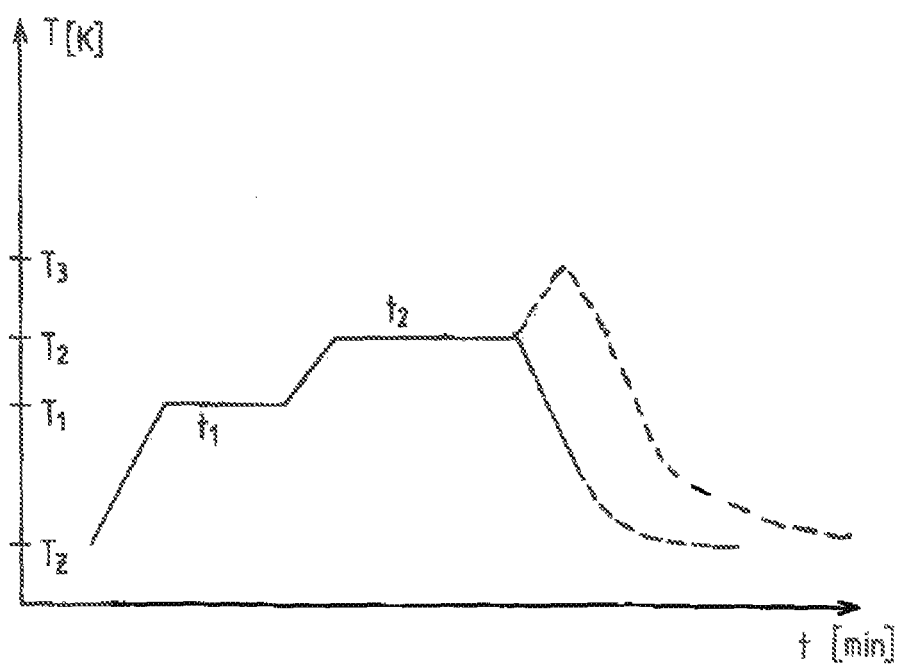
FIG. 3 shows a diagram of temperature as a function of time.

FIG. 3 shows a heating and cooling curve used in the sintering of the sinter products 46. The curve of FIG. 3 applies to an object of larger size that is to be sintered. As example one could mention a dental bridge framework with 4 elements.

According to the minimum basic principle, the sintering furnace and consequently the sintering chamber 12, and consequently also the product to be sintered 46, initially is heated from room temperature $T_z$ to a temperature $T_1$ whereby $T_1$ is between 800° C. and 1100° C. if cobalt-chromium alloys are used as material for the sinter product 46. The heating rate preferably should be between 20 K/min and 80 K/min. The sinter product 46 is held at the temperature $T_1$ for a time period between 1 min and 10 min. Next takes place a heating from the temperature $T_1$ to a temperature $T_2$ between 1200° C. and 1350° C. at a heating rate between 5 K/min and 30 K/min. The sinter product 46 is held at the temperature $T_2$ for a time period $t_2$ between 5 and 120 min and subsequently is cooled to a temperature below 400° C., whereby one must at least choose a cooling rate between 5 K/min and 100 K/min.

Subsequently cooling to room temperature takes place, whereby preferably the device 10, 100 is removed from the sintering chamber 12. For this purpose, the device 10, 100 can be lowered, as is symbolized by the double arrow 52. If required, the sinter product can after cooling to the temperature $T_1$ be held at the temperature $T_1$ for a time period between 1 min and 10 min. This is followed by a cooling to room temperature Tz.

As is evident in the schematic illustration of FIG. 3, after reaching the sintering temperature $T_2$, the sintered product may for a short time period be heated to a higher $T_3$ (dashed region), in order to effect a melting of the surface. The short-term deliberate melting can be performed during the holding time $t_2$, preferably after the holding time $t_2$. The latter is illustrated in FIG. 3.

Heating to the temperature $T_1$, holding at this temperature, and subsequently the further heating to the temperature $T_2$ with possibly deviating heating rate for the sintering of smaller-size objects, such as a framework for a single tooth, is not required. Rather, one can heat directly from room temperature to the temperature $T_2$. Independently hereof, one also has the option after the holding at the temperature $T_2$ to implement a short-term temperature increase to a temperature $T_3$, in order to achieve a melting of the surface of the sintered product.

The invention claimed is:

1. A device for sintering a sinter product, said device comprising:
    a base plate having an opening;
    a cover disposed on the base plate, said cover having a peripheral rim sealingly engaged with the base plate;
    a tray disposed within the cover and arranged on the base plate;
    a capping element covering the tray;
    wherein inner surfaces of the tray and the capping element define a first internal chamber;
    wherein an outer surface of the tray with capping element and an inner surface of the cover define a second internal chamber; and
    wherein the first interior chamber is connected to the second interior chamber in a gas-flow-allowing manner.

2. The device according to claim 1, further comprising a sintering chamber;
    wherein the base plate, cover, tray, and capping element are disposed within the sintering chamber.

3. The device according to claim 1, wherein the rim of the cover rests form-fittingly on the base plate.

4. The device according to claim 1, further comprising a ring disposed on the base plate and supporting the tray, said ring comprising a plurality of openings.

5. The device according to claim 4, wherein an area of the ring covers the opening in the base plate.

6. The device according to claim 1, wherein the tray further comprises a plurality of projections projecting from an underside of the tray, wherein said plurality of projections support the tray on the base plate.

7. The device according to claim 6, wherein three projections are arranged equidistantly on the underside of the base plate.

8. The device of claim 1 wherein the tray is configured to hold the sinter product arranged on a bulk material.

9. The device according to claim 1, wherein the base plate, the cover, the tray, and the capping element are manufactured from SiC or SiN.

10. The device according to claim 1, wherein the second interior chamber is under a pressure burden p sufficient to prevent a lifting of the cover from the tray.

11. The device according to claim 10, wherein 1 mbar≤p≤25 mbar, relative to ambient pressure.

12. The device according to claim 10, wherein 2 mbar≤p≤10 mbar, relative to ambient pressure.

13. The device according to claim 1, wherein the opening in the base plate is configured to connect to a protective-gas supply line, or a protective-gas discharge line.

14. The device according to claim 1, wherein the cover is pot-shaped.

\* \* \* \* \*